US00PP35659P3

(12) United States Plant Patent
Schoone

(10) Patent No.: US PP35,659 P3
(45) Date of Patent: Feb. 20, 2024

(54) ***PHALAENOPSIS* PLANT NAMED 'APRIL SHOWERS'**

(50) Latin Name: *Phalaenopsis hybrida*
Varietal Denomination: April Showers

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/214,519

(22) Filed: Jun. 26, 2023

(65) Prior Publication Data

US 2023/0422648 P1 Dec. 28, 2023

Related U.S. Application Data

(60) Provisional application No. 63/355,878, filed on Jun. 27, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'April Showers', characterized by its upright plant habit; moderately vigorous growth habit; strong flowering stems; strong leaves; freely flowering habit with typically two to three inflorescences per plant, each inflorescence with numerous flowers; white-colored flowers with dark red and dark purplish red-colored stripes and sectors; flowers with white, yellow and purple-colored labella; and good postproduction longevity.

1 Drawing Sheet

Figure 1:
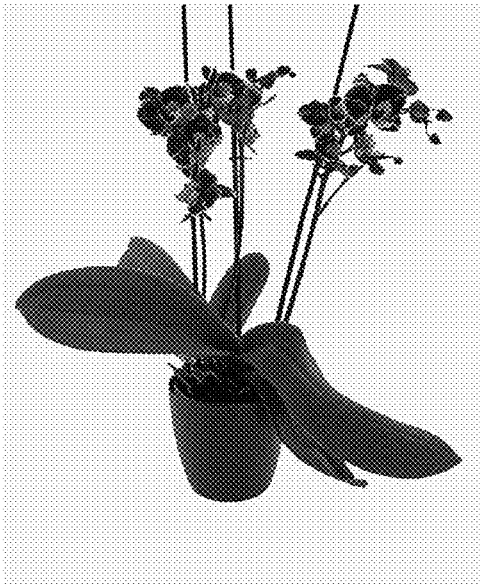

Botanical designation: *Phalaenopsis hybrida.*
Cultivar denomination: 'APRIL SHOWERS'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Aug. 15, 2022, application number 2022/1908. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'April Showers'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in April, 2007 in Assendelft, The Netherlands of *Phalaenopsis hybrida* 'Timothy Christopher', not patented, as the female, or seed, parent with a proprietary selection of *Phalaenopsis hybrida* identified as code number 4551, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in December, 2019.

Asexual reproduction of the new *Phalaenopsis* plant by in vitro meristem propagation in a controlled environment in Assendelft, The Netherlands since December, 2020 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'April Showers'. These characteristics in combination distinguish 'April Showers' as a new and distinct *Phalaenopsis* plant:

1. Upright plant habit.
2. Moderately vigorous growth habit.
3. Strong flowering sterns.
4. Strong leaves.
5. Freely flowering habit with typically two to three inflorescences per plant, each inflorescence with numerous flowers.
6. White-colored flowers with dark red and dark purplish red-colored stripes and sectors.
7. Flowers with white, yellow and purple-colored labella.
8. Good postproduction longevity.

Plants of the new *Phalaenopsis* can be compared to plants of the female parent, 'Timothy Christopher'. Plants of the new *Phalaenopsis* differ primarily from plants of 'Timothy Christopher' in flower petal color as flower petals of plants of the new *Phalaenopsis* are white in color with dark red and dark purplish red-colored stripes and sectors whereas the flower petals of plants of the 'Timothy Christopher' are solid white in color. In addition, the flower labella of plants of the new *Phalaenopsis* are white, yellow and purple in color whereas the flower labella of plants of 'Timothy Christopher' are mostly white in color with some yellow-colored areas.

Plants of the new *Phalaenopsis* can be compared to plants of the male parent selection. Plants of the new *Phalaenopsis* differ primarily from plants of the male parent selection in flower petal color as flower petals of plants of the new *Phalaenopsis* have distinct white-colored edges whereas flower petals of plants of the male parent selection do not have distinct white-colored edges. In addition, flower petals of plants of the new *Phalaenopsis* are imbricate whereas flower petals of plants of the male parent selection are "free" and not imbricate.

Plants of the new *Phalaenopsis* can be compared to plants of *Phalaenopsis hybrida* 'Streetwise', disclosed in U.S. Plant Pat. No. 25,374. In side-by-side comparisons, plants of the new *Phalaenopsis* differ primarily from plants of 'Streetwise' in flower petal color as flower petals of plants of the new *Phalaenopsis* are white in color with dark red and dark purplish red-colored stripes and sectors whereas the flower petals of plants of 'Streetwise' are light yellowish green in color with purple-colored markings. In addition, plants of the new *Phalaenopsis* are more freely flowering than plants of 'Streetwise'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph at the top of the sheet (FIG. 1) is a side perspective view of a typical flowering plant of 'April Showers' grown in a container.

Figure 2:
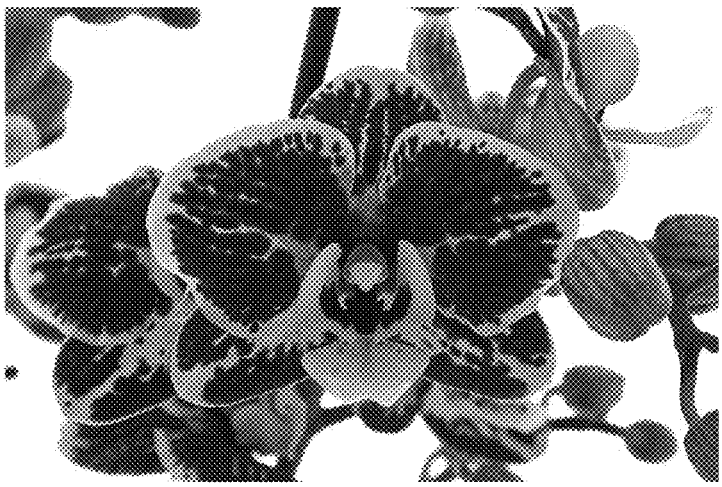

The photograph at the bottom of the sheet (FIG. 2) is a close-up view of typical flowers of 'April Showers'.

DETAILED BOTANICAL DESCRIPTION

The aforementioned photographs and following observations and measurements describe plants grown during the autumn in 8.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27 C. During the final six months of production of the plants, day temperatures ranged from 20 C to 22 C and night temperatures ranged from 18 C to 20 C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'April Showers'.

Parentage:

*Female, or seed, parent.*—*Phalaenopsis hybrida* 'Timothy Christopher', not patented.

*Male parent.*—Proprietary selection of *Phalaenopsis hybrida* identified as code number 4551, not patented.

Propagation:

*Type.*—By in vitro meristem propagation.

*Time to initiate roots, summer and winter.*—About two weeks at temperatures about 28 C to 30 C.

*Time to produce a rooted young plant, summer and winter.*—About 20 to 25 weeks at temperatures about 28 C to 30 C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form in and growth habit.*—Herbaceous epiphyte; upright plant habit with typically two to three inflorescences per plant, each inflorescence with numerous flowers; monopodial; moderately vigorous growth habit and moderate growth rate.

*Plant height, substrate level to top of foliar plane.*—About 11.2 cm.

*Plant height, substrate level to top of inflorescences.*—About 28 cm.

*Plant diameter or spread.*—About 31.1 cm.

Leaf description:

*Arrangement and quantity.*—Distichous, simple; sessile; about four leaves per plant.

*Length.*—About 18.6 cm.

*Width.*—About 7.8 cm.

*Aspect.*—Outwardly arching.

*Shape.*—Narrowly obovate to narrowly elliptic-oblong; slightly carinate.

*Apex.*—Unequal acute.

*Base.*—Sheathing. Sheath length: About 1.8 cm. Sheath width: About 1.1 cm. Sheath color: Close to 144B to 144C; towards the margins, close to 143B.

*Margin.*—Entire; not undulate.

*Texture and luster, upper surface.*—Smooth, glabrous; slightly glossy.

*Texture and luster, lower surface.*—Smooth, glabrous; moderately glossy.

*Venation pattern.*—Camptodromous.

*Color.*—Developing leaves, upper surface: Close to 137A. Developing leaves, lower surface: Close to 146A; margin edges, close to N186C. Fully expanded leaves, upper surface: Close to a blend of 137B and 146A; venation, close to NN137B. Fully expanded leaves, lower surface: Close to a blend of 146B and 146C; margin edges, close to 199A; venation, close to 137A.

Inflorescence description:

*Appearance and flowering habit*.—Showy zygomorphic flowers arranged on axillary simple or branched racemes; typically two to three inflorescences per plant; each inflorescence with about 14 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about ten weeks on the plant; flowers not persistent.

*Inflorescence length* (*lowermost flower to inflorescence apex*).—About 15.7 cm.

*Inflorescence width*.—About 12.6 cm.

*Flower buds*.—Height: About 1.6 cm. Diameter: About 1.2 cm by 1.4 cm. Shape: Broadly ovate. Color: Close to 151A; venation, close to a blend of 178A and 183B.

*Flower size*.—About 5.4 cm (vertical) by 5.6 cm (horizontal).

*Flower depth*.—About 4.4 cm.

*Petals, quantity and arrangement*.—Three, two lateral petals and one center petal transformed into a labellum.

*Lateral petals*.—Length: About 2.7 cm. Width: About 3.1 cm. Shape: Roughly reniform. Apex: Obtuse to rounded. Margin: Entire; moderately and finely undulate. Texture and luster, upper and lower surfaces: Smooth, glabrous, velvety; matte. Color: When opening, upper surface: Close to N155B and NN155D; towards the base, close to N78D; heavily blotched and marbled with close to N79B, N79C and 187A to 187C. When opening, lower surface: Close to 156C, 156D and 157B; towards the margins, close to N155B to N155C; moderately to heavily blotched with close to 187B and 187C. Fully opened, upper surface: Close to NN155D; towards the base, close to N78D; heavily blotched and marbled with close to 60A, N79B, N79C and 187A to 187B; color does not change with subsequent development. Fully opened, lower surface: Close to 76C; towards the margins, close to N155A; moderately to heavily blotched with close to 77A and N79C; color does not change with subsequent development.

*Labella*.—Appearance: Three-parted with two lateral lobes and a central lobe. Length, lateral lobes: About 1.7 cm. Width, lateral lobes: About 1 cm. Length, central lobe: About 1.9 cm. Width, central lobe: About 5 mm to 16 mm. Length, Cirrhose tips: About 5 mm. Shape, lateral lobes: Obovate. Shape, central lobe: Deltoid with a slightly elongated apex. Apex, lateral lobes: Obtuse. Apex, central lobe: Cleft with two curved cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 4.5 mm in width and about 3 mm in height. Color: When opening, upper surface: Lateral lobes: Close to NN155D; towards the base, close to 59A and 59B; towards the margins, close to 5C. Central lobe: Close to 4A to 4B; sparsely dotted, close to 181B; narrow area, close to NN155B; cirrhose tips, close to NN155B; towards the base, close to a blend of 79A and N186B. Callosities: Close to a blend of 79A and N186B. When opening, lower surface: Lateral lobes: Close to NN155D; towards the base, close to 76B; towards the margins, close to 5C. Central lobe: Close to 4A to 4B; moderately dotted, close to 70A and 70B; narrow area, close to NN155B; cirrhose tips, close to NN155B; towards the base, close to 197D. Fully opened, upper surface: Lateral lobes: Close to NN155D; towards the base, close to 59A and 59B; towards the margins, close to 6B to 6C. Central lobe: Close to 10A; sparsely dotted, close to 181B; narrow area, close to NN155B; cirrhose tips, close to NN155B; towards the base, close to a blend of 79A and N186B. Callosities: Close to a blend of 79A and N79A. Fully opened, lower surface: Lateral lobes: Close to NN155D; towards the base, close to 76B; towards the margins, close to 7B. Central lobe: Close to 4A; moderately dotted, close to 70A and 70B; narrow area, close to NN155B; cirrhose tips, close to NN155B; towards the base, close to 197D.

*Sepals*.—Quantity and arrangement: Three, one upper dorsal sepal and two lower lateral sepals. Length, dorsal sepal: About 2.8 cm. Width, dorsal sepal: About 2.2 cm. Length, lateral sepals: About 2.8 cm. Width, lateral sepals: About 1.9 cm. Shape, dorsal sepal: Broadly elliptic. Shape, lateral sepals: Ovate. Apex, dorsal sepal: Shallowly and broadly retuse. Apex, lateral sepals: Acute to obtuse. Base, dorsal and lateral sepals: Truncate. Margin, dorsal and lateral sepals: Entire. Texture and luster, dorsal and lateral sepals, upper surface: Smooth, glabrous, moderately velvety; matte. Texture and luster, dorsal and lateral sepals, lower surface: Smooth, glabrous, slightly velvety; slightly glossy. Color, dorsal sepal: When opening, upper surface: Close to NN155B; towards the base, close to N78C and N78D; heavily blotched and marbled with close to N79B, N79C and 187A to 187C. When opening, lower surface: Close to 195B; towards the margins, close to 75C and 75D and heavily blotched with close to N186C and N186D; venation, close to N186C and N186D. Fully opened, upper surface: Close to NN155D; towards the base, close to N78C, N78D and NN78A; heavily blotched and marbled with close to 60A and N79A to N79C; color does not change with subsequent development. Fully opened, lower surface: Close to N155B; towards the base, close to 157D; towards the margins, close to 71A and N79C; venation, close to N186D; color does not change with subsequent development. Color, lateral sepals: When opening, upper surface: Close to 157C; towards the base, close to 157A; heavily blotched and marbled with close to N79B, N79C and 187A to 187C. When opening, lower surface: Close to 160A and 160B; towards the margins, heavily blotched with close to N186D and 187A; venation, close to N186D and 187A. Fully opened, upper surface: Close to 157D; towards the base, close to 157B; heavily blotched and marbled with close to 71A and N79B, N79C and N186D; color does not change with subsequent development. Fully opened, lower surface: Close to 75D and 157A; towards the base, close to N170D; heavily blotched, close to N186D; venation, close to N186D; color does not change with subsequent development.

*Peduncles*.—Length: About 28.8 cm. Diameter: About 4.5 mm. Strength: Strong. Aspect: Upright to outwardly arching. Texture and luster: Smooth, glabrous; matte. Color: Close to 148A; moderately to densely covered with fine dots and marbling, close to 138A and 138B.

*Pedicels*.—Length: About 2.7 cm. Diameter: About 2.5 mm. Strength: Moderately strong. Aspect: About 65 degrees from peduncle axis. Texture and luster: Smooth, glabrous; matte. Color: Upper surface: Close to 187B to 187C; distally, close to 75C. Lower surface: Close to 145C; distally, close to 157D.

*Reproductive organs*.—Androecium: Column length: About 8 mm. Column width: About 5 mm. Column color: Close to N78B; distally, close to a blend of N78A and N79C. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to 76C; margins, close to 77B. Ovary length: About 5 mm. Ovary diameter: About 1 mm. Ovary color: Close to 147D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40 C and are suitable for USDA Hardiness Zones 10 to 12.

It is claimed:

1. A new and distinct *Phalaenopsis* plant named 'April Showers' as illustrated and described.

* * * * *